United States Patent [19]
Behr et al.

[11] Patent Number: 4,592,911
[45] Date of Patent: Jun. 3, 1986

[54] EXTRACTION OF CAMOMILE WITH LIQUID CARBON DIOXIDE

[75] Inventors: Norbert Behr, Burgthann; Othmar von Ettingshausen, Düsseldorf; Reinhold Wüst, Kaarst; Henk van der Mei, deceased, late of Rinteln, all of Fed. Rep. of Germany, by Jannette van der Mei née Reek, executrix

[73] Assignee: Degussa Aktiengesellschaft, Frankfurt, Fed. Rep. of Germany

[21] Appl. No.: 618,765

[22] Filed: Jun. 11, 1984

Related U.S. Application Data

[63] Continuation of Ser. No. 348,308, Feb. 12, 1982, abandoned.

[30] Foreign Application Priority Data

Feb. 16, 1981 [DE]   Fed. Rep. of Germany ....... 3105557

[51] Int. Cl.$^4$ ............................................. A61K 35/78
[52] U.S. Cl. .................................................. 424/195.1
[58] Field of Search ........... 23/293 R; 424/364, 195.1; 426/424, 425, 651

[56] References Cited

U.S. PATENT DOCUMENTS

| | | | |
|---|---|---|---|
| 3,477,856 | 11/1969 | Schultz | 426/424 |
| 3,966,981 | 6/1976 | Schultz | 426/425 |
| 4,282,259 | 8/1981 | Whelddon et al. | 426/425 |
| 4,338,348 | 7/1982 | Muller | 426/651 |

FOREIGN PATENT DOCUMENTS

| | | |
|---|---|---|
| 2709033 | 9/1978 | Fed. Rep. of Germany . |
| 2827602 | 9/1980 | Fed. Rep. of Germany . |
| 351889 | 10/1972 | U.S.S.R. ............................. 426/425 |

OTHER PUBLICATIONS

Schultz et al, Liquid Carbon Dioxide for Selective Aroma Extraction; Food Technology, vol. 24, pp. 1282 et seq., Nov. 1970.
Schultz et al, Pilot-Plant Extraction with Liquid CO$_2$, Food Technology; vol. 28; Jun. 1974, pp. 32 et seq.

*Primary Examiner*—Hiram H. Bernstein
*Attorney, Agent, or Firm*—Cushman, Darby & Cushman

[57] ABSTRACT

Extraction of commercially useful aromatic substances, fragrances and medicinal products from camomile is accomplished using liquid carbon dioxide. Good yields of heat labile components are obtained by this process.

7 Claims, No Drawings

EXTRACTION OF CAMOMILE WITH LIQUID CARBON DIOXIDE

This application is a continuation of application Ser. No. 348,308, filed Feb. 12, 1982 and now abandoned.

BACKGROUND OF THE INVENTION

Camomile, the dried flower heads of *Matricicaria chamomilla L.*, Compositae, and/or *Anthemis nobilis L.*, Compositae, contains a number of commercially useful aromatic substances, fragrances, and medicinal products which are very sensitive to even mildly elevated temperatures. For example, when camomile tea is prepared in the home by pouring hot water over the dried flower heads, the resulting tea contains only a fraction of those substances originally present in the camomile, the rest having been destroyed by heat. Furthermore, some of the substances present in the tea have low solubility in water so that a significant portion of these substances will remain in the flower heads. Accordingly, the use of warm or hot water as an extraction solvent for commercial use is not feasible.

When organic solvents are used as the extraction medium for camomile, a number of disadvantages result. For example, traces of the organic solvents will remain in the extract, and are almost impossible to separate quantitatively from the extract.

One prior art method used to recover camomile substances using a milder extraction procedure is disclosed in German Patent DE-OS No. 27 09 033, wherein a non-toxic gas such as carbon dioxide, with the gas in the supercritical state, is used to extract the camomile. However, where supercritical gases are used, a temperature above the critical temperature of the gas must be employed. When carbon dioxide is the gas selected, the temperature must be maintained above 31.06° C., which is its critical temperature. Supercritical gas was chosen in that process since in the supercritical state both the density of the gas and solubility of substances in the gas can be considerably increased when high extraction pressures are used. However, due to the extreme sensitivity to even slightly elevated temperatures of some of the substances in camomile, particularly proazulenes such as matricin, this prior art extraction method is not without its drawbacks.

Liquid carbon dioxide has been used in certain prior art extraction processes. A survey of the state of the art can be found in W. G. Schultz et al. in "Food Technology", Vol. 24, 1282 et seg, (1970) and Vol. 28, 32 et seg. (1974). As can be seen from these literature references, extractions with liquid carbon dioxide are used for coffee, spices, and to extract aromatic substances from fruits. German Patent DE-AS No. 28 27 002 discloses an extraction process using liquid carbon dioxide for hops. However, for the extraction of camomile, only the above-mentioned process using supercritical carbon dioxide is known.

DESCRIPTION OF THE INVENTION

It has now been found that the use of liquid carbon dioxide at a temperature below the critical temperature for carbon dioxide, and using a pressure up to 400 bar above the saturation pressure of the carbon dioxide at the temperature chosen, results in a high yield of camomile extract, with its heat labile substances intact.

The liquid range of carbon dioxide extends from $-56°$ to $+31°$ C., and a temperature within this range may be utilized in the practice of the invention. Preferably, however, a temperature in the range of from about 0° C. to about 31° C. is chosen. As stated above, the pressure can range up to about 400 bar, preferably from about 100 bar to about 300 bar, above the saturation pressure of the carbon dioxide at the temperature selected.

Separation of the camomile extract from the liquid carbon dioxide can be accomplished by utilizing an expansion vessel. Decreases in pressure and/or changes in temperature (keeping in mind the heat labile nature of certain components of the extract) are employed to separate the extract from the liquid carbon dioxide. Preferably, a temperature is selected that is either at or below the temperature of the liquid carbon dioxide used for the extraction step, and a pressure is selected which is the saturation pressure for carbon dioxide at the particular temperature chosen. In this manner, a two phase system forms in the expansion vessel consisting of gaseous, extract-free carbon dioxide, and the liquid extract containing a small quantity of carbon dioxide. Preferably, the gaseous, extract-free carbon dioxide is then compressed to a liquid and returned to the extraction vessel at the pressure used therein. In this manner, the carbon dioxide is recovered for reuse in the process of the invention. The process can also be made continuous wherein liquid carbon dioxide containing camomile extract is continuously drawn off, introduced into an expansion chamber, and the gaseous, extract-free carbon dioxide is compressed and returned to the extraction stage at a continuous controlled rate.

The present process offers many advantages over prior art processes for extracting substances from camomile. First of all, the thermo-labile substances are extracted intact in high yield. Extraction times are relatively short, e.g. of the order of 3 to 5 hours. The use of a co-solvent such as water is not needed. Aromatic substances as well as fragrances and medicinal substances are simultaneously and completely isolated at low temperatures, thereby eliminating growth of bacteria and fungi.

Interestingly, when elevated extraction pressures for the liquid carbon dioxide are utilized in the practice of the invention, i.e. extraction pressures above its saturation pressure, quantitative extractions and relatively short extraction times can be achieved as discussed above. Since increasing the pressure of liquid carbon dioxide results in only an insignificant increase in its density, no significant improvement in dissolving ability should result. In fact, in the survey by W. G. Schultz in Food Technology, cited above, all of the sources cited perform extractions at the saturation pressure of the liquid carbon dioxide.

The discovery that liquid carbon dioxide can be used in accordance with the process of the invention is itself unexpected. Literature on the use of liquid carbon dioxide as a solvent always teaches its selectivity as a solvent, namely that it will selectively dissolve esters, aldehydes and ketones, as well as certain other compounds that do not have a molecular weight in excess of about 150. Many substances contained in camomile, such as matricin, bisabolol, and flavonoids, have molecular weights greater than 150, and also contain free hydroxyl groups. Surprisingly, the present process is effective in solubilizing these compounds in the liquid carbon dioxide.

The invention will be better understood from the following examples which are given for illustration purposes only and not to limit the invention.

EXAMPLE I (a) Substrate: dried camomile flowers, German (chamomillae flos)
(b) Extraction conditions (batch process):

| | |
|---|---|
| extraction temperature: | 29° C. |
| extraction pressure: | 130 bar |
| extraction time: | 3 hours |

(c) Separation conditions:

| | |
|---|---|
| temperature: | 22° C. |
| pressure: | about 60 bar |

(d) Yield:

| | |
|---|---|
| total extract: | 1.4% by weight of substrate |
| essential oil: | 0.5 ml/100 g of substrate |
| α-bisobolol: | 1.3 ppm of substrate |
| matricin: | 350 ppm of substrate |
| en-in-dicycloether: | 1450 ppm |

EXAMPLE II (a) Substrate: dried camomile flowers, German (chamomillae flos)
(b) Extraction conditions (batch process):

| | |
|---|---|
| extraction temperature: | 28° C. |
| extraction pressure: | 260 bar |
| extraction time: | 5 hours |

(c) Separation conditions: same as in EXAMPLE I.

(d) Yield:

| | |
|---|---|
| total extract: | 2.2% by weight of substrate |
| essential oil | 0.7 ml/100 g of substrate |
| α-bisobolol | 1.9 ppm of substrate |
| matricin | 350 ppm of substrate |
| en-in-dicycloether | 1490 ppm of substrate |

What is claimed is:

1. A process for extracting heat labile substances having a molecular weight in excess of 150 from camomile comprising the steps of:
    (a) contacting camomile with liquid carbon dioxide maintained at a pressure of from about 100 bar to about 400 bar above the saturation pressure of the carbon dioxide at the contact temperature for a contact time of from about 3 to about 5 hours and thereby extracting from the camomile heat labile substances having a molecular weight in excess of 150 including matricin, bisabolol and flavonoids; and
    (b) separating the liquid carbon dioxide from the camomile extract dissolved therein by adjusting the pressure and/or temperature to gasify the liquid carbon dioxide.

2. A process according to claim 1 wherein the carbon dioxide in step (a) is maintained at a pressure in the range of from about 100 to about 300 bar.

3. A process according to claim 1 wherein the gaseous carbon dioxide obtained from step (b) is compressed to liquid carbon dioxide and returned to step (a).

4. A process according to claim 3 wherein the process is a continuous process.

5. A process according to claim 1 wherein step (b) is carried out by adjusting the pressure to the saturation pressure for carbon dioxide at the temperature selected.

6. A process according to claim 5 wherein the temperature selected in step (b) is at or below the temperature selected for step (a).

7. A process according to claim 1 wherein the liquid carbon dioxide in step (a) is maintained at a temperature in the range of from about 0° to about 31° C.

* * * * *